(12) United States Patent
Smelt et al.

(10) Patent No.: US 9,290,629 B2
(45) Date of Patent: *Mar. 22, 2016

(54) PROCESS FOR PRODUCING HIGH MOLECULAR WEIGHT POLYETHYLENE

(71) Applicant: DSM IP ASSETS B.V., Heerlen (NL)

(72) Inventors: Harold Jan Smelt, Sittard (NL); Pieter Gijsman, Beek (NL); Martin Van Duin, Sittard (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/670,742

(22) Filed: Mar. 27, 2015

(65) Prior Publication Data

US 2015/0203641 A1    Jul. 23, 2015

Related U.S. Application Data

(63) Continuation of application No. 12/741,431, filed as application No. PCT/EP2008/065089 on Nov. 6, 2008.

(30) Foreign Application Priority Data

Nov. 6, 2007   (EP) .................................... 07120102
Nov. 6, 2007   (EP) .................................... 07120108

(51) Int. Cl.
| C08F 2/46 | (2006.01) |
| C08L 23/06 | (2006.01) |
| C08K 5/3435 | (2006.01) |
| C08K 3/28 | (2006.01) |
| C08J 3/28 | (2006.01) |
| A61L 27/16 | (2006.01) |
| C08K 5/3492 | (2006.01) |

(52) U.S. Cl.
CPC .. *C08J 3/28* (2013.01); *A61L 27/16* (2013.01); *C08K 5/3435* (2013.01); *C08K 5/34926* (2013.01); *C08L 23/06* (2013.01); *C08J 2323/36* (2013.01)

(58) Field of Classification Search
USPC ......................................................... 524/237
See application file for complete search history.

(56) References Cited

U.S. PATENT DOCUMENTS 3,513,151 A * 5/1970 Santiago ........................ 526/106
3,883,631 A * 5/1975 Murray ........................ 264/210.2
3,975,481 A * 8/1976 Baumgaertner ............... 264/126
4,233,412 A * 11/1980 Rody et al. ...................... 525/167

(Continued)

FOREIGN PATENT DOCUMENTS

| EP | 0946635 | 5/2003 |
| JP | 2004-501232 | 1/2004 |

(Continued)

OTHER PUBLICATIONS

Notice of Reasons of Rejection, JP Appln. P2010-531549 (Jul. 30, 2013).

(Continued)

*Primary Examiner* — Peter A Salamon
(74) *Attorney, Agent, or Firm* — Nixon & Vanderhye P.C.

(57) ABSTRACT

The invention relates to a process for producing an (ultra) high molecular weight polyethylene (HMWPE) article comprising:
  incorporating into the HMWPE resin a Hindered Amine Light Stabilizer (HALS) and
  cross-link the (U)HMWPE during or after molding the (U)HMWPE resin.
In particular the invention relates to a process comprising the following steps:
  a) incorporating into (U)HMWPE resin a Hindered Amine Light Stabilizer (HALS) according to one of the following general formulas or combinations hereof:

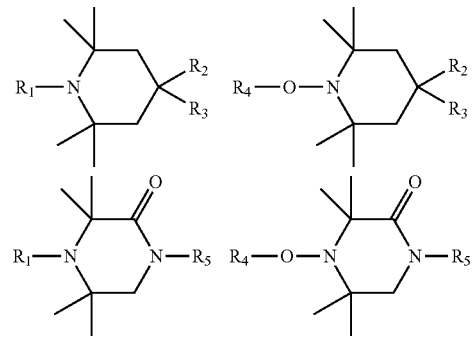

wherein $R_1$ up to and including $R_5$ are herein independent substituents; for example containing hydrogen, ether, ester, amine, amide, alkyl, alkenyl, alkynyl, aralkyl, cycloalkyl and/or aryl groups, which substituents may in turn contain functional groups, for example alcohols, ketones, anhydrides, imines, siloxanes, ethers, carboxyl groups, aldehydes, esters, amides, imides, amines, nitriles, ethers, urethanes and any combination thereof;
  b) molding the (U)HMWPE resin comprising the HALS, resulting in an article;
  c) cross-linking and sterilizing the article via gamma radiation or electron beam radiation;
  d) optionally, if step b results in a stock shape, machining the stock shape into an article;
wherein step c and step d can be performed in either order.

23 Claims, No Drawings

(56) References Cited

U.S. PATENT DOCUMENTS

| | | | |
|---|---|---|---|
| 4,281,070 A * | 7/1981 | Scheetz et al. | 524/528 |
| 5,414,049 A * | 5/1995 | Sun et al. | 525/333.7 |
| 5,428,079 A * | 6/1995 | Bastiaansen et al. | 522/161 |
| 5,597,854 A * | 1/1997 | Birbaum et al. | 524/100 |
| 5,702,657 A * | 12/1997 | Yoshida et al. | 264/112 |
| 6,265,504 B1 * | 7/2001 | Liu et al. | 526/161 |
| 6,329,465 B1 * | 12/2001 | Takahashi et al. | 525/191 |
| 6,344,505 B1 * | 2/2002 | Valentine et al. | 524/91 |
| 6,579,601 B2 * | 6/2003 | Kollaja et al. | 428/212 |
| 6,664,317 B2 * | 12/2003 | King, III | 524/99 |
| 6,670,412 B1 * | 12/2003 | Erderly et al. | 524/156 |
| 6,818,020 B2 * | 11/2004 | Sun et al. | 623/23.58 |
| 7,030,196 B2 * | 4/2006 | Roth et al. | 525/375 |
| 7,999,038 B2 * | 8/2011 | Honda et al. | 525/191 |
| 2002/0086924 A1 * | 7/2002 | King, III | 524/237 |
| 2003/0195282 A1 * | 10/2003 | King, III | 524/236 |
| 2003/0212161 A1 * | 11/2003 | McKellop et al. | 522/3 |
| 2005/0059750 A1 * | 3/2005 | Sun et al. | 522/161 |
| 2007/0077375 A1 * | 4/2007 | Honda et al. | 428/31 |
| 2010/0144930 A1 | 6/2010 | Dirix et al. | |

FOREIGN PATENT DOCUMENTS

| | | |
|---|---|---|
| WO | WO 01/85843 | 11/2001 |
| WO | WO 2005/065911 | 7/2005 |
| WO | WO 2006/041969 | 4/2006 |

OTHER PUBLICATIONS

International Search Report for PCT/EP2008/065089, mailed Jun. 30, 2009.

Yan Qing et al., "Photoinitiated Crosslinking of low Density Polyethylene. III: Degradation and Stabilization of PhotoCrosslinked Polyethylene", Polymer Engineering & Science, Wiley, Hoboken, NJ, US, vol. 34, No. 5, Mar. 15, 1994, pp. 446-452, XP000500447.

Yan Qing et al., Polymer Engineering & Science, vol. 31, No. 22, Nov. 1, 1991, pp. 1561-1566, XP002531497.

Yan Qing et al., Polymer Engineering & Science, vol. 31, No. 22, Nov. 1, 1991, pp. 1567-1571, XP002531498.

Written Opinion of the International Searching Authority for PCT/EP2008/065089, mailed Jun. 30, 2009.

* cited by examiner

PROCESS FOR PRODUCING HIGH MOLECULAR WEIGHT POLYETHYLENE

This application is a continuation of U.S. application Ser. No. 12/741,431 filed May 5, 2010 which is the U.S. national phase of International Application No. PCT/EP2008/065089, filed Nov. 6, 2008, which designated the U.S. and claims priority to EP Application No. 07120102.4, filed Nov. 6, 2007 and EP Patent Application No. 07120108.1, filed Nov. 6, 2007, the entire contents of each of which are hereby incorporated by reference.

The present invention relates to a process for producing an (ultra) high molecular weight polyethylene ((U)HMWPE) article. The present invention further relates to an (U)HMWPE article obtainable by said process, use of an article in a medical application, and to the use of stabilizers for the stabilization of (U)HMWPE.

Excellent properties in terms of wear, fatigue and fracture resistance have made (U)HMWPE the material of choice in orthopedics, especially the fabrication of articular components for arthroplastry, for which a high wear resistance is required. The acetubular cup or liner in a total hip joint replacement and the tibial insert in a total knee joint replacement are important applications of (U)HMWPE.

HMWPE is herein defined as a substantially linear ethylene homopolymer or copolymer with a weight average molecular weight (Mw) of $3.10^5$ g/mol or more, a molecular weight distribution ($M_w/M_n$) of between 2 and 18 and an intrinsic viscosity (IV) of 1,5-8 dl/g. Preferably, the IV of HMWPE is 3-8 dl/g and more preferably, 5-8 dl/g. The IV is defined according to ISO 1628-3. UHMWPE is herein defined as a substantially linear ethylene homopolymer or copolymer with a weight average molecular weight (Mw) of $10^6$ g/mol or more, a molecular weight distribution ($M_w/M_n$) of between 2 and 18 and an IV of 8 dl/g or more. Preferably, the IV of UHMWPE is between 8 and 60 dl/g.

(U)HMWPE can be obtained by any known process for the production of (U)HMWPE, as described by for example Steven M. Kurtz in "The UHMWPE Handbook", Elsevier Academic Press, 2004, p. 14-22. (U)HMWPE is generally obtained as a powder which can further be processed by molding and machining as described below.

Studies have shown that cross-linking of (U)HMWPE with gamma or electron beam rays is highly effective against wear, which was most clearly demonstrated for smooth counter-faces, such as those generally involved in a prosthetic coupling.

However, despite the outstanding success of the use of (cross-linked) (U)HMWPE in total joint replacement surgery, failures arising from, for example, aseptic loosening or mechanical failure of the component after few years of implantation are still quite frequent, as shown in J. H. Dumbleton et al., J. Arthroplasty 2002, 17(5): 649-661 and T. W. Bauer et al., Skeletal Radiol 1999, 28(9): 483-497.

It has been demonstrated that most of the failures were to be ascribed to the wear of the (U)HMWPE component. Wear is a major concern, since wear leads to the formation of debris, which in turn induces an inflammatory response, causing loosening of the implant.

It has been found that the failure of the components due to is at least partly due to a reduction of the oxidative stability of (U)HMWPE, which is a side-effects of irradiation used for cross-linking and/or sterilization. Irradiation was found to induce, in addition to cross-linking which has a positive effect on the mechanical properties, oxidative degradation of polyethylene which has a negative effect on the mechanical properties of (U)HMWPE.

To overcome this problem, irradiated (U)HMWPE is often annealed and remelted to reduce the amount of free radicals. However, these treatments have a negative effect on the mechanical properties, such as the yield and the ultimate strength.

In EP-0995450B1 vitamin E is coated on UHMWPE powder to avoid oxidation of the UHMWPE as a result of sterilization by gamma radiation. Coating is accomplished by impregnating the UHMWPE powder with a solution comprising vitamin E followed by evaporation of the solvent. Subsequently the impregnated product is molded and machined into an implant which is irradiated with gamma radiation.

Disadvantages of using vitamin E as an anti-oxidant are that:
  it results in the undesired side-effect of yellowing the (U)HMWPE. Yellowed (U)HMWPE is perceived as an aged product in the market,
  it is consumed during cross-linking, having a negative effect on the cross-linking efficiency and
  it has to be used in a relatively large amount to be effective against oxidative degradation of the (U)HMWPE that occurs after cross-linking of the (U)HMWPE.

A primary object of the invention is therefore to at least provide an alternative process for the production of an (U)HMWPE article. In particular it is an object of the invention to provide a process resulting in a (U)HMWPE article which is less yellow, comprises, preferably, a smaller amount of stabilizer and preferably has at least the same stability and mechanical properties as the (U)HMWPE article of the prior art.

Surprisingly, it was found that the object of the invention can be reached by providing a process for producing an (ultra) high molecular weight polyethylene ((U)HMWPE) article comprising:
  incorporating into the (U)HMWPE resin a Hindered Amine Light Stabilizer (HALS) and
  cross-link the (U)HMWPE during or after molding the (U)HMWPE resin.

In a first embodiment of the invention the process for producing an (U)HMWPE article can comprise the following steps:
  a) incorporating into (U)HMWPE resin a Hindered Amine Light Stabilizer (HALS) according to one of the following general formulas or combinations hereof:

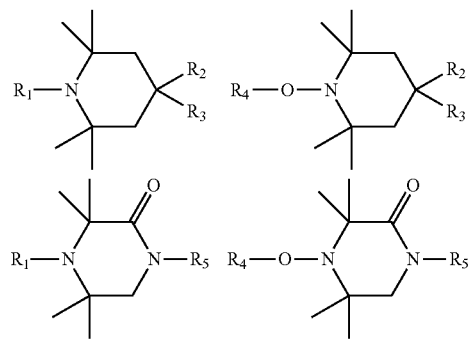

wherein $R_1$ up to and including $R_5$ are herein independent substituents; for example containing hydrogen, ether, ester, amine, amide, alkyl, alkenyl, alkynyl, aralkyl, cycloalkyl and/or aryl groups, which substituents may in turn contain functional groups, for example alcohols, ketones, anhydrides, imines, siloxanes, ethers, carboxyl groups, aldehydes, esters, amides, imides, amines, nitriles, ethers, urethanes and any combination thereof;
  b) molding or extruding the (U)HMWPE resin comprising the HALS, resulting in an article;
  c) cross-linking and sterilizing the article via gamma radiation or electron beam radiation;
  d) optionally, if step b results in a stock shape, machining the stock shape into an article;
wherein step c and step d can be performed in either order.

In a second embodiment of the invention the process for producing an (U)HMWPE article can comprise the following steps:
  a) incorporating into (U)HMWPE resin a Hindered Amine Light Stabilizer (HALS) according to one of the following general formulas or combinations hereof:

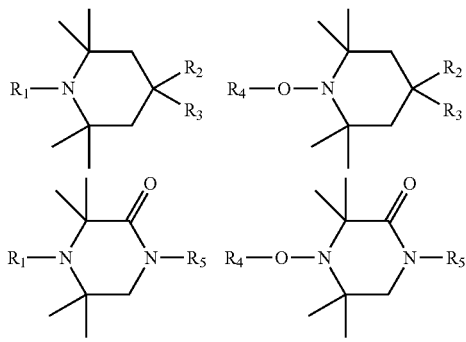

wherein $R_1$ up to and including $R_5$ are herein independent substituents; for example containing hydrogen, ether, ester, amine, amide, alkyl, alkenyl, alkynyl, aralkyl, cycloalkyl and/or aryl groups, which substituents may in turn contain functional groups, for example alcohols, ketones, anhydrides, imines, siloxanes, ethers, carboxyl groups, aldehydes, esters, amides, imides, amines, nitriles, ethers, urethanes and any combination thereof;
  b) adding a an initiator, for example a peroxide, and optionally a coagent;
  c) molding or extruding the (U)HMWPE resin comprising the HALS and the initiator, resulting in a stock shape or an article;
  d) optionally, when further cross-linking or sterilizing via gamma radiation or electron beam radiation is applied, cross-linking and/or sterilizing the stock shape or the article;
  e) optionally, if step c results in a stock shape, machining the stock shape into an article;
wherein step d and step e can be performed in either order.

Surprisingly, a much lower amount of the HALS can be used compared with the amount of vitamin E for stabilizing the (U)HMWPE article.

The HALS is preferably used in an amount of between 0.001 and 5% by weight, more preferably between 0.01 and 2% by weight, most preferably between 0.02 and 1% by weight, based on the total weight of the (U)HMWPE.

Preferably, the HALS chosen is a compound derived from a substituted piperidine compound, in particular any compound which is derived from an alkyl-substituted piperidyl, piperidinyl or piperazinone compound or a substituted alkoxypiperidinyl compound.

Examples of such compounds are: 2,2,6,6-tetramethyl-4-piperidone; 2,2,6,6-tetramethyl-4-piperidinol; bis-(1,2,2,6,6-pentamethylpiperidyl)-(3',5'-di-tert-butyl-4'-hydroxybenzyl) butylmalonate; di-(2,2,6,6-tetramethyl-4-piperidyl) sebacate (Tinuvin® 770); oligomer of N-(2-hydroxyethyl)-2,2,6,6-tetramethyl-4-piperidinol and succinic acid (Tinuvin® 622); bis-(2,2,6,6-tetramethyl-4-piperidinyl) succinate; bis-(1-octyloxy-2,2,6,6-tetramethyl-4-piperidinyl) sebacate (Tinuvin® 123); bis-(1,2,2,6,6-pentamethyl-4-piperidinyl) sebacate (Tinuvin® 765); N,N'-bis-(2,2,6,6-tetramethyl-4-piperidyl) hexane-1,6-diamine (Chimassorb T5); N-butyl-2,2,6,6-tetramethyl-4-piperidinamine; 2,2'-[(2,2,6,-tetramethylpiperidinyl)imino]bis-[ethanol]; poly((6-morpholine-S-triazine-2,4-diyl)(2,2,6,6-tetramethyl-4-piperidinyl)-iminohexamethylene-(2,2,6,6-tetramethyl-4-iperidinyl)-imino) (Cyasorb® UV 3346); 5-(2,2,6,6-tetramethyl-4-piperidinyl)-2-cycloundecyloxazole) (Hostavin® N20); 8-acetyl-3-dodecyl-7,7,9,9-tetramethyl-1,3,8-triaza-spiro(4,5)decane-2,4-dione; polymethylpropyl-3-oxy[4(2,2,6,6-tetramethyl)-piperidinyl)siloxane (Uvasil® 299); copolymer of α-methylstyrene-N-(2,2,6,6-tetramethyl-4-piperidinyl)maleimide and N-stearylmaleimide; 1,2,3,4-butanetetracarboxylic acid, polymer with beta, beta, beta', beta'-tetramethyl-2,4,8,10-tetraoxaspiro[5.5]undecane-3,9-diethanol, 1,2,2,6,6-pentamethyl-4-piperidinyl ester (Mark® LA63); 2,4,8,10-tetraoxaspiro[5.5]undecane-3,9-diethanol, beta,beta,beta',beta'-tetramethyl-, polymer with 1,2,3,4-butanetetracarboxylic acid, 2,2,6,6-tetramethyl-4-piperidinyl ester (Mark® LA68); D-glucitol, 1,3:2,4-bis-O-(2,2,6,6-tetramethyl-4-piperidinylidene)-(HALS 7); oligomer of 7-oxa-3,20-diazadispiro[5.1.11.2]heneicosan-21-one,2,2,4,4-tetramethyl-20-(oxiranylmethyl) (Hostavin® N30); propanedioic acid, [(4-methoxyphenyl)methylene]-,bis(1,2,2,6,6-pentamethyl-4-piperidinyl) ester (Sanduvor® PR 31); formamide, N,N'-1,6-hexanediylbis[N-(2,2,6,6-tetramethyl-4-piperidinyl (Uvinul® 4050H). 1,3,5-triazine-2,4,6-triamine, N,N'''-[1,2-ethanediylbis[[[4,6-bis[butyl(1,2,2,6,6-pentamethyl-4-iperidinyl)amino]-1,3,5-triazine-2-yl]imino]-3,1-propanediyl]]-bis[N',N'''-dibutyl-N',N'''-bis(1,2,2,6,6-pentamethyl-4-piperidinyl) (Chimassorb® 119); 1,5-dioxaspiro (5,5) undecane 3,3-dicarboxylic acid, bis (2,2,6,6-tetramethyl-4-peridinyl) ester (Cyasorb® UV-500); 1,5-dioxaspiro (5,5) undecane 3,3-dicarboxylic acid, bis (1,2,2,6,6-pentamethyl-4-peridinyl) ester (Cyasorb® UV-516); N-2,2,6,6-tetramethyl-4-piperidinyl-N-amino-oxamide; 4-acryloyloxy-1,2,2,6,6-pentamethyl-4-piperidine; HALS PB-41 (Clariant Huningue S.A.); 1,3-benzendicarboxamide,N,N'-bis(2,2,6,6-tetramethyl-4-piperidinyl) (Nylostab® S-EED (Clariant Huningue S. A.)); 3-dodecyl-1-(2,2,6,6-tetramethyl-4-piperidyl)-pyrrolidin-2,5-dione; 1,3-Propanediamine, N,N-1,2-ethanediylbis-,polymer with 2,4,6-trichloro-1,3,5-triazine, reaction products with N-butyl-2,2,6,6-tetramethyl-4-piperidinamine (Uvasorb® HA88); 1,1'-(1,2-ethane-di-yl)-bis-(3,3',5,5'-tetra-methyl-piperazinone) (Good-rite® 3034); 1,1',1"-(1,3,5-triazine-2,4,6-triyltris ((cyclohexylimino)-2,1-ethanediyl)tris(3,3,5,5-tetramethylpiperazinone); (Good-rite® 3150); 1,1",1"-(1,3,5-triazine-2,4,6-triyltris((cyclohexylimino)-2,1-ethanediyl)tris(3,3,4,5,5-tetramethylpiperazinone) (Good-rite® 3159); 1,2,3,4-Butanetetracarboxylic acid, tetrakis(2,2,6,6-tetramethyl-4-piperidinyl) ester (ADK STAB@ LA-57) 1,2,3,4-Butanetetra-carboxylic acid, 1,2,3-tris-(1,2,2,6,6-penta-methyl-4-piperidyl)-4-tridecylester (ADK STAB® LA-62).

Mixture of esters of 2,2,6,6-tetra-methyl-4-pipiridinol and several fatty acid (CYASORB® UV3853); Propanedioic acid, [(4-methoxyphenyl)methylene]-,bis(2,2,6,6-tetramethyl-4-piperidinyl) ester (HOSTAVIN® PR-31); 3-Dodecyl-1-(2,2,6,6-tetramethyl-4-piperidyl)-pyrrolidin-2,5-dione (CYASORB® UV3581); 3-Dodecyl-1-(1,2,2,6,6-pentamethyl-4-piperidyl)-pyrrolidin-2,5-dione (CYASORB®

UV3641); 1,2,3,4-Butanetetracarboxylic acid, tetrakis(1,2,2,6,6-pentamethyl-4-piperidinyl)ester (ADK STAB® LA-52); 1,2,3,4-Butane-tetra-carboxylic acid, 1,2,3-tris-(2,2,6,6-tetra-methyl-4-piperidyl)-4-tridecylester (ADK STAB® LA-67); Mixture of: 2,2,4,4 tetramethyl-21-oxo-7-oxa-3.20-diazadispiro[5.1.11.2]-heneicosane-20-propionic acid dodecylester and 2,2,4,4 tetramethyl-21-oxo-7-oxa-3.20-diazadispiro[5.1.11.2]-heneicosane-20-propionicacid tetradecylester (Hostavin® N24); Poly[[6-[(1,1,3,3-tetramethylbutyl)amino]-s-triazine-2,4-diyl][2,2,6,6-tetramethyl-4-piperidinyl)-imino]hexamethylene[(2,2,6,6-tetramethyl-4-piperidinyl) imino]]}(Chimassorb® 944); 1,3,5-Triazine-2,4,6-triamine, N,N'''-[1,2-ethanediylbis[[[4,6-bis[butyl(1,2,2,6,6-pentamethyl-4-piperidinyl)amino]-1,3,5-triazine-2-yl]imino]-3,1-propanediyl]]-bis[N',N''-dibutyl-N',N''-bis(1,2,2,6,6-pentamethyl-4-piperidinyl) (Chimassorb® 119); Poly[(6-morpholino-s-triazine-2,4-diyl)[1,2,2,6,6-penta-methyl-4-piperidyl)imino]-hexamethylene[(1,2,2,6,6 penta-methyl-4-piperidyl)imino]]1,6-Hexanediamine, N,N'-bis(1,2,2,6,6-pentamethyl-4-pipiridinyl)-, Polymers with morpholine-2,4,6-trichloro-1,3,5-triazine (CYASORB® UV3529); Poly-methoxypopyl-3-oxy[4(1,2,2,6,6-pentamethyl)-piperidinyl]-siloxane (Uvasil®816); 1,6-Hexanediamine, N,N'-bis(2,2,6,6-tetramethyl-4piperidinyl)-polymer with 2,4,6-trichloro-1,3,5-triazine, reaction products with N-butyl-1-butanamine and N-butyl-2,2,6,6-tetramethyl-4-piperidinamine (Chimassorb® 2020); Reaction products of N,N'-ethane-1,2-diylbis (1,3-propanediamine), cyclohexane, peroxidized 4-butylamino-2,2,6,6-tetramethylpiperidine and 2,4,6-trichloro-1,3,5-triazine (Flamestab NOR® 116); 1,6-hexanediamine, N,N'-bis(2,2,6,6-tetramethyl-4-piperidinyl)-, polymer with 2,4,6-trichloro-1,3,5-triazine, reaction products with 3-bromo-1-propene, n-butyl-1-butanamine and N-butyl-2,2,6,6-tetramethyl-4-piperidinamine, oxidised, hydrogenated (Tinuvin NOR® 371).

Preferably, the HALS has a molecular mass of 1000 g/mol or more, more preferably 1500 g/mol or more, or contains a group via which it can be grafted to the (U)HMWPE. Both measures help to avoid leaching of the stabilizer from the product during use.

The HALS can be incorporated in (U)HMWPE by any known method. The HALS, either as liquid or powder, can be mixed with the (U)HMWPE resin or with the (U)HMWPE melt. Alternatively, (U)HMWPE resin may be impregnated with a solution of the HALS, or a solution of the HALS may be sprayed on the (U)HMWPE resin. Also (U)HMWPE particles may be mixed with the HALS in supercritical $CO_2$.

Dependent on the HALS type, examples of suitable solvents include methanol, ethanol, butanol, isopropyl alcohol, ethylglycol, ethyl acetate, tetrahydrofuran, acetone, methyl-isobutylketone, chloroform, methylene chloride, hexane, toluene, and xylene. Further the HALS stabilizer can be incorporated in the (U)HMWPE during polymerization. This has the advantage that a very homogeneous distribution of the HALS in the (U)HMWPE can be obtained.

According to one embodiment of the invention the (U)HMWPE is cross-linked by irradiation by applying for example gamma irradiation or electron beam irradiation, as described in the above-referenced "The UHMWPE Handbook" on p. 37-47. The irradiation dose used to obtain a highly cross-linked (U)HMWPE article is chosen between 30 and 250 kGray (kGy), preferably between 30 and 170 kGy and more preferably between 40 and 130 kGy. To obtain a lower cross-linked (U)HMWPE article or when irradiation is used in combination with chemical cross-linking by the use of an initiator a lower irradiation dose can be used, from for instance 25 to 50 kGy.

For sterilization of the (U)HMWPE article according to the invention an irradiation dose between 10 and 40 kGy, preferably between 20 and 35 kGy can be used.

According to a second embodiment of the invention the (U)HMWPE is cross-linked by adding an initiator, for example a peroxide, and optionally a coagent to the (U)HMWPE.

Examples of suitable peroxides include tert-butyl cumyl peroxide, tert-butyl peroxybenzoate, di-tert-butyl peroxide, 3,3,5,7,7-pentamethyl-1,2,4-trioxepane,1,1-di(tert-butylperoxy)-3,3,5-trimethylcyclohexane, butyl 4,4-di(tert-butylperoxy)valerate, 2,5-dimethyl-2,5-di(tert-butylperoxy)hexyne-3,2,5-dimethyl-2,5-di(tert-butylperoxy)hexane, di(4-methylbenzoyl) peroxide, dibenzoyl peroxide, di(2,4-dichlorobenzoyl) peroxide, dicumyl peroxide, 3,3,5,7,7-pentamethyl-1,2,4-trioxepane, 1-(2-tert.-butylperoxyisopropyl)-3-isopropenyl benzene, 2,4-diallyloxy-6-tert-butylperoxy-1,3,5-triazine, di(tert-butylperoxyisopropyl)benzene, diisopropylbenzene monohydroperoxide, cumyl hydroperoxide, and tert-butyl hydroperoxide.

Optionally a coagent, a compound with 2 or more unsaturations, is used to enhance the peroxide cross-linking efficiency. Examples of suitable coagents include divinylbenzene, diallylphthalate, triallylcyanurate, triallylisocyanuarate, triallyltrimellitate, meta-phenylene bismaelimide, ethyleneglycol dimethacrylate, ethyleneglycol diacrylate, trimethylopropane timethacrylate, trimethylopropane, timethacrylate, pentaerytritol tetramethacrylate, zinc diacrylate, zinc dimethacrylate, and polybutadiene.

The initiator is generally used in an amount of between 0.001 and 2.5% by weight, preferably between 0.01 and 1% by weight, and the co-agent in an amount of between 0.001 and 2.5% by weight, preferably between 0.1 and 1% by weight, both based on the total weight of the (U)HMWPE.

The HALS, optionally the initiator, for example peroxide, and optionally the coagent, can be incorporated in the (U)HMWPE in step a and optionally b, and then be consolidated by compression molding or hot isostatic pressing. The HALS, optionally the initiator and optionally the coagent can be incorporated in (U)HMWPE by any known method. The HALS, optionally the initiator and optionally the coagent, either as liquid or powder, can be mixed with the (U)HMWPE resin or melt. Alternatively, (U)HMWPE resin may be impregnated with a solution of the HALS and optionally the initiator in a solvent, spraying a solution of the HALS and optionally the initiator on (U)HMWPE resin, and mixing (U)HMWPE particles with the HALS and optionally the initiator in supercritical $CO_2$. In all methods the impregnation of the HALS and optionally the initiator may take place simultaneously or separately, i.e. one after the other.

Cross-linking takes place in the melt during molding and/or via radiation. Several processing methods can be used for molding and, if necessary, machining (optional step) of (U)HMWPE resins into bulk products, as described in for example Steven M. Kurtz in "The UHMWPE Handbook", Elsevier Academic Press, 2004, p. 22-31 (hereinafter "The UHMWPE Handbook"), which is incorporated herein as a reference. A short description of the main methods is described below.

The first method is compression molding, wherein a mold filled with (U)HMWPE resin is subjected to a combination of high temperature and high pressure for a certain amount of time. Subsequently the system is cooled at a slow and uniform rate in order to minimize shrinkage and deformation of the product. The product is than machined into smaller blocks or cylindrical bars from which the final components, for example articular components, can be machined.

The second method, ram extrusion, produces cylindrical bar stock shapes ranging in diameter from 25 mm to 150 mm. In this process, the (U)HMWPE resin charge is fed into a channel and then heat is applied. A ram then compresses and extrudes the plasticized powder charge into the heated cylindrical barrel, where it is consolidated into a cylindrical bar stock. As the ram moves back and forward, the powder stock in the chamber is refilled. The final components, for example articular components, can be machined from the bar stock.

In the third method, direct compression molding, the (U)HMWPE resin charge is consolidated into a final or semi-final bulk product using a pre-shaped mold. Machining is not always necessary when this method is applied. Although this process is slow and costly, orthopedic articular components made using this method have very smooth surface finishes and excellent dimensional consistency.

A HMWPE resin can also be melt processed by injection molding or extrusion into a sheet or a bar. In this way the end product can be directly obtained, but machining the product to obtain the end product is also possible.

In addition to the above methods Hot Isostatic Pressing (HIPing) can be applied, as described in The UHMWPE Handbook on p. 27.

Machining of (U)HMWPE consists of milling and turning operations for both first rough and finishing steps. More details about machining are provided in the above-referenced "The UHMWPE Handbook" on p. 31-32.

The methods that are used for cross-linking (U)HMWPE by radiation, and which can also be applied to (U)HMWPE stabilized with the HALS and, or optionally, chemically cross-linked according to the invention, are gamma irradiation and electron beam irradiation, as described by G. Lewis in Biomaterials 2001, 22: 371-401. With gamma irradiation, the dosage used ranges from 20-1000 kGy. Either a stock shape or an article, or both, can be subjected to irradiation cross-linking applying electron beam or gamma radiation.

Optionally, the stock shape or article is annealed after cross-linking at a temperature below the melting temperature of (U)HMWPE, for example between 60 and 140° C.

In addition to ethylene, (U)HMWPE may comprise one or more comonomers, for example propylene, butane, pentene, hexane, 4-methylpentene, octane, octadiene and vinylnorbornene, and the like, to achieve improved processing characteristics or alter the physical and mechanical properties of the polymer. Furthermore the polymer can contain non-polymer materials such as reinforcing agents, fillers, flame retardants, pigments, and other auxiliary additives like plasticizers, processing aids, such as mould release agents, further stabilizers such as antioxidants and UV stabilizers, crystallization accelerating agents or nucleating agents, impact modifiers and compatibilizers. In particular, an inorganic stearate such as calcium or zinc stearate may be added to the (U)HMWPE-P resin as a flow agent or to minimize the effect of any catalyst residues, which have a potential for corroding the conversion machines. Moreover, calcium stearate may act as a lubricant when a part is to be fabricated using ram-extrusion of the polymer powders, and may help the product to maintain its white color.

The (U)HMWPE article comprising a HALS has a cross-link density of 0.09 mol/dm$^3$ or more.

The (U)HMWPE article according to the invention can be applied in medical applications, preferably in implants which have a thickness of at least 2 mm, more preferably at least 4 mm. For example the implants can be used in orthopedics as bearing material in artificial joints. (U)HMWPE can be used in for example hip arthroplasty, knee replacements, shoulder replacements and spinal applications such as total disc replacement. These applications are described in detail in the above-referenced "The UHMWPE Handbook" in Chapters 4-6 (hip), 7-8 (knee), 9 (shoulder) and 10 (spinal applications).

The present invention will now be described in detail with reference to the following examples that by no means limit the scope of the invention.

EXAMPLES

Materials

UHMWPE:
  The used UHMWPE had an Intrinsic Viscosity, measured according to ISO 1628-3, of 27 dl/g, which corresponds with a molecular weight of 7.3 million g/mol, as calculated using Margolies equation Mw=53700×[I.V]$^{1.49}$
  The average particle size of the used UHMWPE resin according to ISO 13320 was 157 micron.
Stabilizers:
  Vitamin E; (Alpha tocopherol from DSM Nutrional Products)
  Poly{[[6-[(1,1,3,3-tetramethylbutyl)amino]-s-triazine-2,4-diyl][(2,2,6,6-tetramethyl-4-piperidinyl)imino]-hexamethylene [(2,2,6,6-tetramethyl-4-piperidinyl)imino]]}; (Chimassorb® 944 from Ciba Specialty Chemicals)
  1,3,5-Triazine-2,4,6-triamine, N,N'''-1,2-ethanediylbis[[[4,6-bis[butyl(1,2,2,6,6-pentamethyl-4-piperidinyl)amino]-1,3,5-triazine-2-yl]imino]-3,1-propanediyl]]-bis[N',N''-dibutyl-N',N''-bis(1,2,2,6,6-pentamethyl-4-piperidinyl); (Chimassorb® 119 from Ciba Specialty Chemicals)
  1,6-hexanediamine, N,N'-bis(2,2,6,6-tetramethyl-4-piperidinyl)-, polymer with 2,4,6-trichloro-1,3,5-triazine, reaction products with 3-bromo-1-propene, n-butyl-1-butanamine and N-butyl-2,2,6,6-tetramethyl-4-piperidinamine, oxidised, hydrogenated; (Tinuvin® NOR 371 from Ciba Specialty Chemicals)
Preparation of Solvent Blended Compounds
  The stabilizers were added to the UHMWPE by solvent blending. The stabilizers were first added to the polymer as a solution in Chloroform (about 100 ml/100 gr polymer); in a second step the chloroform was evaporated.
Irradiation of the Samples
  Irradiation was performed by gamma irradiation (dose 25, 75 and 150 kGray (kGy)) on stock samples under nitrogen that were vacuum sealed into paper bags with an aluminum coating on the inside. To prepare the test samples for the Swell test a stock sample was prepared that was irradiated and was later machined into the smaller test samples.
Preparation of the Samples
  Powder was compression molded into samples according to ISO 11542-2.
  Needed sample dimensions for analyses were machined from the molded stock samples.
Ageing:
  The samples for the tensile test and for color determination were aged during two weeks in an air venting oven (Binder FDL115) at 110° C.
Cross-Link Density Measurement
  The cross-link density was determined according to ASTM F2214-02, using samples with the dimensions 5 mm*5 mm*5 mm that were machined out of stock samples that were irradiated. These samples were subjected to swelling in o-xylene.

Colour Determination

Colour determination was done according to ISO 7724-1-2-3 (CIELAB, D65, 10°, d8). The determination was done in reflection using a black background with a Minolta spectrophotometer. As samples 1 mm thick plaques were used that were machined out of the stock samples after irradiation and ageing.

Tensile Tests

The tensile tests (elongation at break and ultimate tensile strength) were performed according to ISO 527.

Tensile bars (Type ISO 527-5B) were punched from 1 mm thick samples, that were machined out of stock samples after irradiation and ageing.

Oxidation Index Determination

The oxidation indices were determined from the Infrared Spectra measured in transmission on coupes of about 100 µm, which were cut from cubes of 5*5*5 mm. The spectra were recorded on a Perkin Elmer Auto Image using 20 scans and a resolution of 4 cm$^{-1}$. The spectra were normalized as in ASTM F2102-06 to 1370 cm$^{-1}$ (1330-1370, base 1400 cm$^{-1}$). The oxidation index was defined as the peak height at 1717 cm$^{-1}$ using a baseline drawn from 1680-1765 cm$^{-1}$.

Results:

TABLE 1

Color determination
In table 1 the difference between the color of the b*-value of the different samples and the color of the reference sample (not stabilized, not irradiated sample) is given.

| | | Radiation dose | | | |
|---|---|---|---|---|---|
| Example | Stabilizer | 0 kGy | 25 kGy | 75 kGy | 150 kGy |
| A | — | 0 | 0.55 | 1.35 | 2.88 |
| B | 0.15 wt % Vitamin E | 7.71 | 12.16 | 12.07 | 13.07 |
| 1 | 0.05 wt % Chimassorb 944 | −0.14 | 0.47 | 1.39 | 3.00 |
| 2 | 0.15 wt % Chimassorb 944 | −0.13 | 0.30 | 1.31 | 2.92 |
| 3 | 0.05 wt % Chimassorb 119 | −0.21 | 0.41 | 1.31 | 2.84 |
| 4 | 0.15 wt % Chimassorb 119 | −0.23 | 0.2 | 1.23 | 2.91 |
| 5 | 0.05 wt % Tinuvin NOR 371 | 0.36 | 0.46 | 1.48 | 2.93 |
| 6 | 0.15 wt % Tinuvin NOR 371 | 0.94 | 1.44 | 2.29 | 3.41 |

From these results it was clear that the Vitamin E containing samples were more yellow than the HALS containing samples.

TABLE 2

Cross-link density
Cross-link density (Mol/dm$^3$) for samples that were irradiated with different doses.

| | | Radiation dose | | |
|---|---|---|---|---|
| Example | Stabilizer | 25 kGy | 75 kGy | 150 kGy |
| C | — | 0.148 | 0.223 | 0.234 |
| D | 0.15 wt % Vitamin E | 0.087 | 0.160 | 0.215 |
| 7 | 0.05 wt % Chimassorb 944 | 0.145 | 0.258 | 0.335 |
| 8 | 0.15 wt % Chimassorb 944 | 0.157 | 0.233 | 0.381 |
| 9 | 0.05 wt % Chimassorb 119 | 0.114 | 0.213 | 0.196 |
| 10 | 0.15 wt % Chimassorb 119 | 0.131 | 0.187 | 0.248 |
| 11 | 0.05 wt % Tinuvin NOR 371 | 0.151 | 0.209 | 0.279 |
| 12 | 0.15 wt % Tinuvin NOR 371 | 0.120 | 0.162 | 0.323 |

From the results in Table 2 it is clear that for the HALS stabilized samples a lower radiation dose is needed to get a cross-link density that is comparable with the Vitamin E containing sample.

TABLE 3

Tensile strength
Tensile strength (N/mm$^2$) of samples that were irradiated with different doses, after ageing for two weeks at 110° C.

| | | Radiation dose | | | |
|---|---|---|---|---|---|
| Example | Stabilizer | 0 kGy | 25 kGy | 75 kGy | 150 kGy |
| E | — | 11.6 | 10.8 | 13.6 | 17.4 |
| F | 0.15 wt % Vitamin E | 55 | 51 | 48.7 | 41.6 |
| 13 | 0.05 wt % Chimassorb 944 | 56.9 | 50.3 | 45.9 | 42.4 |
| 14 | 0.05 wt % Chimassorb 119 | 55.4 | 49.6 | 45.3 | 41.8 |
| 15 | 0.05 wt % Tinuvin NOR 371 | 56.2 | 48.5 | 45.1 | 40.6 |

From these results it was clear that after ageing samples comprising 0.05 wt % HALS had a tensile strength that was comparable with a tensile strength for a sample comprising 0.15 wt % Vitamin E.

TABLE 4

Oxidation index
Oxidation index of samples that were irradiated with different doses after ageing for two weeks at 110° C.

| | | Radiation dose | | | |
|---|---|---|---|---|---|
| Example | Stabilizer | 0 kGy | 25 kGy | 75 kGy | 150 kGy |
| G | — | 9.74 | 8.96 | 10.5 | 8.8 |
| H | 0.15 wt % Vitamin E | 0.012 | 0.042 | 0.095 | 0.215 |
| 16 | 0.05 wt % Chimassorb 944 | 0.112 | 0.019 | 0.184 | 0.239 |
| 17 | 0.05 wt % Chimassorb 119 | 0.024 | 0.139 | 0.276 | 0.210 |
| 18 | 0.05 wt % Tinuvin NOR 371 | 0.108 | 0.212 | 0.224 | 0.293 |

From these results it was clear that 0.05 wt % HALS could prevent an increase of the oxidation index. The amount needed from the HALS was lower than the 0.15 wt % Vitamin E that was needed to obtain the same result.

TABLE 5

Change in cross-link density
Change in cross-link density (in mol/dm$^3$) of samples that were irradiated with different doses after ageing for two weeks at 110° C.

| | | Radiation dose | |
|---|---|---|---|
| Example | Stabilizer | 25 kGy | 75 kGy |
| I | — | −0.1 | −0.2 |
| J | 0.15 wt % Vitamin E | 0.0 | 0.0 |
| 19 | 0.05 wt % Chimassorb 944 | 0.0 | 0.0 |
| 20 | 0.05 wt % Chimassorb 119 | 0.0 | 0.0 |
| 21 | 0.05 wt % Tinuvin NOR 371 | 0.0 | 0.0 |

From these results it was clear that the HALS, as well as Vitamin E, were effective in preventing a decrease in cross-link density due to ageing.

The invention claimed is:

1. A process for producing an (ultra)high molecular weight polyethylene ((U)HMWPE) article comprising:
    (a.) forming a composition by incorporating a stabilizer consisting of one or more Hindered Amine Light Stabilizers selected from the group consisting of 2,2,6,6-tetramethyl-4-piperidone; 2,2,6,6-tetramethyl-4-piperidinol; bis-(1,2,2,6,6-pentamethylpiperidyl)-(3',5'-di-tert-butyl-4'-hydroxybenzyl) butylmalonate; di-(2,2,6,6-tetramethyl-4-piperidyl) sebacate; oligomer of N-(2-hydroxyethyl)-2,2,6,6-tetramethyl-4-piperidinol and succinic acid; bis-(2,2,6,6-tetramethyl-4-piperidinyl)

succinate; bis-(1-octyloxy-2,2,6,6-tetramethyl-4-piperidinyl) sebacate; bis-(1,2,2,6,6-pentamethyl-4-piperidinyl) sebacate; N,N'-bis-(2,2,6,6-tetramethyl-4-piperidyl) hexane-1,6-diamine; N-butyl-2,2,6,6-tetramethyl-4-piperidinamine; 2,2'-[(2,2,6,6-tetramethylpiperidinyl)imino]-bis-[ethanol]; poly((6-morpholine-S-triazine-2,4-diyl)(2,2,6,6-tetramethyl-4-piperidinyl)-iminohexamethylene-(2,2,6,6-tetramethyl-4-piperidinyl)-imino); 5-(2,2,6,6-tetramethyl-4-piperidinyl)-2-cycloundecyloxazole); 8-acetyl-3-dodecyl-7,7,9,9-tetramethyl-1,3,8-triazaspiro(4,5)decane-2,4-dione; polymethylpropyl-3-oxy[4(2,2,6,6-tetramethyl)piperidinyl)siloxane; copolymer of α-methylstyrene-N-(2,2,6,6-tetramethyl-4-piperidinyl)maleimide and N-stearylmaleimide; 1,2,3,4-butanetetracarboxylic acid, polymer with beta,beta,beta',beta'-tetramethyl-2,4,8,10-tetraoxaspiro[5.5]undecane-3,9-diethanol, 1,2,2,6,6-pentamethyl-4-piperidinyl ester; 2,4,8,10-tetraoxaspiro[5.5]undecane-3,9-diethanol, beta,beta,beta',beta'-tetramethyl-, polymer with 1,2,3,4-butanetetracarboxylic acid, 2,2,6,6-tetramethyl-4-piperidinyl ester; D-glucitol, 1,3:2,4-bis-O-(2,2,6,6-tetramethyl-4-piperidinylidene)-; oligomer of 7-oxa-3,20-diazadispiro[5.1.11.2]heneicosan-21-one,2,2,4,4-tetramethyl-20-(oxiranylmethyl); propanedioic acid, [(4-methoxyphenyl)methylene]-bis(1,2,2,6,6-pentamethyl-4-piperidinyl) ester; formamide, N,N'-1,6-hexanediylbis[N-(2,2,6,6-tetramethyl-4-piperidinyl; 1,3,5-triazine-2,4,6-triamine, N,N'''-[1,2-ethanediylbis[[[4,6-bis[butyl(1,2,2,6,6-pentamethyl-4-iperidinyl)amino]-1,3,5-triazine-2-yl]imino]-3,1-propanediyl]]-bis[N',N''-dibutyl-N',N''-bis(1,2,2,6,6-pentamethyl-4-piperidinyl); 1,5-dioxaspiro (5,5) undecane 3,3-dicarboxylic acid, bis (2,2,6,6-tetramethyl-4-piperidinyl) ester; 1,5-dioxaspiro (5,5) undecane 3,3-dicarboxylic acid, bis (1,2,2,6,6-pentamethyl-4-peridinyl) ester; N-2,2,6,6-tetramethyl-4-piperidinyl-N-amino-oxamide; 4-acryloyloxy-1,2,2,6,6-pentamethyl-4-piperidine; 1,3-benzenedicarboxamide, N,N'-bis(2,2,6,6-tetramethyl-4-piperidinyl); 3-dodecyl-1-(2,2,6,6-tetramethyl-4-piperidyl)-pyrrolidin-2,5-dione; 1,3-Propanediamine, N,N-1,2-ethanediylbis-, polymer with 2,4,6-trichloro-1,3,5-triazine, reaction products with N-butyl-2,2,6,6-tetramethyl-4-piperidinamine; 1,1'-(1,2-ethane-di-yl)-bis-(3,3',5,5'-tetra-methyl-piperazinone); 1,1',1''-(1,3,5-triazine-2,4,6-triyltris((cyclohexylimino)-2,1-ethanediyl)tris(3,3,5,5-tetramethylpiperazinone); 1,1',1''-(1,3,5-triazine-2,4,6-triyl-tris((cyclohexylimino)-2,1-ethanediyl)tris(3,3,4,5,5-tetramethylpiperazinone); 1,2,3,4-Butanetetracarboxylic acid, tetrakis(2,2,6,6-tetramethyl-4-piperidinyl) ester; 1,2,3,4-Butane-tetracarboxylic acid, 1,2,3-tris-(1,2,2,6,6-penta-methyl-4-piperidyl)-4-tridecylester; mixture of esters of 2,2,6,6-tetra-methyl-4-pipiridinol and several fatty acids; Propanedioic acid, [(4-methoxyphenyl)methylene]-,bis (2,2,6,6-tetramethyl-4-piperidinyl) ester; 3-Dodecyl-1-(2,2,6,6-tetramethyl-4-piperidyl)-pyrrolidin-2,5-dione; 3-Dodecyl-1-(1,2,2,6,6-pentamethyl-4-piperidyl)-pyrrolidin-2,5-dione; 1,2,3,4-Butanetetracarboxylic acid, tetrakis(1,2,2,6,6-pentamethyl-4-piperidinyl)ester; 1,2,3,4-Butane-tetra-carboxylic acid, 1,2,3-tris-(2,2,6,6-tetra-methyl-4-piperidyl)-4-tridecylester; mixture of: 2,2,4,4 tetramethyl-21-oxo-7-oxa-3.20-diazadispiro [5.1.11.2]-heneicosane-20-propionic acid dodecylester and 2,2,4,4 tetramethyl-21-oxo-7-oxa-3.20-diazadispiro[5.1.11.2]-heneicosane-20-propionicacid tetradecylester; Poly[[6-[(1,1,3,3-tetramethylbutyl)amino]-s-triazine-2,4-diyl][2,2,6,6-tetramethyl-4-piperidinyl)-imino]hexamethylene[(2,2,6,6-tetramethyl-4-piperidinyl) iminol]}; 1,3,5-Triazine-2,4,6-triamine, N,N'''-[1,2-ethanediylbis[[[4,6-bis[butyl(1,2,2,6,6-pentamethyl-4-piperidinyl)amino]-1,3,5-triazine-2-yl]imino]-3,1-propanediyl]]-bis[N',N''-dibutyl-N',N''-bis(1,2,2,6,6-pentamethyl-4-piperidinyl); Poly[(6-morpholino-s-triazine-2,4-diyl)[1,2,2,6,6-penta-methyl-4-piperidyl)imino]-hexamethylene[(1,2,2,6,6 penta-methyl-4-piperidyl)iminol]1,6-Hexanediamine, N,N'-bis(1,2,2,6,6-pentamethyl-4-pipiridinyl)-, Polymers with morpholine-2,4,6-trichloro-1,3,5-triazine; Poly-methoxypopyl-3-oxy[4(1,2,2,6,6-pentamethyl)-piperidinyl]-siloxane; 1,6-Hexanediamine, N,N'-bis(2,2,6,6-tetramethyl-4-piperidinyl)-polymer with 2,4,6-trichloro-1,3,5-triazine, reaction products with N-butyl-1-butanamine and N-butyl-2,2,6,6-tetramethyl-4-piperidinamine; reaction products of N,N'-ethane-1,2-diylbis (1,3-propanediamine), cyclohexane, peroxidized 4-butylamino-2,2,6,6-tetramethylpiperidine and 2,4,6-trichloro-1,3,5-triazine; and 1,6-hexanediamine, N,N'-bis(2,2,6,6-tetramethyl-4-piperidinyl)-, polymer with 2,4,6-trichloro-1,3,5-triazine, reaction products with 3-bromo-1-propene, n-butyl-1-butanamine and N-butyl-2,2,6,6-tetramethyl-4-piperidinamine, oxidized, hydrogenated into a (U)HMWPE resin having a molecular weight distribution (Mw/Mn) of between 2 and 18, wherein Hindered Amine Light Stabilizers are the only stabilizers in the composition; and (b.) cross-linking the composition during or after molding by irradiating the composition with an irradiation dose of from 30 to 250 kGy, thereby forming an article with a cross-link density of 0.09 mol/dm$^3$ or more.

2. The process according to claim 1, wherein the one or more Hindered Amine Light Stabilizers comprise N,N'''-[1, 2-ethanediylbis[[[4,6-bis[butyl(1,2,2,6,6-pentamethyl-4-iperidinyl)amino]-1,3,5-triazine-2-yl]imino]-3,1-propanediyl]]bis[N',N''-dibutyl-N',N''-bis(1,2,2,6,6-pentamethyl-4-piperidinyl) or poly{[[6[(1,1,3,3-tetramethylbutyl)amino]-s-triazine-2,4-diyl][(2,2,6,6-tetramethyl-4-piperidinyl)imino]-hexamethylene[(2,2,6,6-tetramethyl-4-piperidinyl)imino]]}.

3. The process according to claim 1, wherein the composition consists of (U)HMWPE resin having a molecular weight distribution (Mw/Mn) of between 2 and 18 and poly {[[6-[(1,1,3,3-tetramethylbutyl)amino]-s-triazine-2,4-diyl][(2,2,6,6-tetramethyl-4-piperidinyl)imino]-hexamethylene [(2,2,6,6-tetramethyl-4-piperidinyl)imino]]}.

4. The process according to claim 1, wherein the (U)HMWPE resin has an intrinsic viscosity of 8 dl/g or more.

5. The process according to claim 1, wherein the one or more Hindered Amine Light Stabilizers are incorporated into the (U)HMWPE resin by mixing the one or more Hindered Amine Light Stabilizers with the (U)HMWPE resin or a melt of the (U)HMWPE resin, by impregnating the (U)HMWPE resin with a solution comprising the one or more Hindered Amine Light Stabilizers, or by spraying a solution comprising the one or more Hindered Amine Light Stabilizers on the (U)HMWPE resin.

6. The process according to claim 1, wherein the Hindered Amine Light Stabilizers are present in an amount between 0.02 and 1% by weight, based on the total weight of the composition.

7. The process according to claim 3, wherein the Hindered Amine Light Stabilizers are present in an amount between 0.02 and 1% by weight, based on the total weight of the composition.

8. The process according to claim 1, wherein the irradiation dose is between 40 and 130 kGy.

9. The process according to claim 2, wherein the irradiation dose is between 40 and 130 kGy.

10. The process according to claim 3, wherein the irradiation dose is between 40 and 130 kGy.

11. The process according to claim 7, wherein the irradiation dose is between 40 and 130 kGy.

12. An artificial medical implant comprising an article formed by the process according to claim 1.

13. An artificial medical implant comprising an article formed by the process according to claim 2.

14. An artificial medical implant comprising an article formed by the process according to claim 3.

15. An artificial medical implant comprising an article formed by the process according to claim 7.

16. An artificial medical implant comprising an article formed by the process according to claim 8.

17. An artificial medical implant comprising an article formed by the process according to claim 10.

18. An artificial medical implant comprising (U)HMWPE and a stabilizer consisting of at least one Hindered Amine Light Stabilizer selected from the group consisting of 2,2,6, 6-tetramethyl-4-piperidone; 2,2,6,6-tetramethyl-4-piperidinol; bis-(1,2,2,6,6-pentamethylpiperidyl)-(3',5'-di-tert-butyl-4'-hydroxybenzyl) butylmalonate; di-(2,2,6,6-tetramethyl-4-piperidyl) sebacate; oligomer of N-(2-hydroxyethyl)-2,2,6,6-tetramethyl-4-piperidinol and succinic acid; bis-(2,2,6,6-tetramethyl-4-piperidinyl) succinate; bis-(1-octyloxy-2,2,6,6-tetramethyl-4-piperidinyl) sebacate; bis-(1,2,2,6,6-pentamethyl-4-piperidinyl) sebacate; N,N'-bis-(2,2,6,6-tetramethyl-4-piperidyl) hexane-1,6-diamine; N-butyl-2,2,6,6-tetramethyl-4-piperidinamine; 2,2'-[(2,2,6,6-tetramethylpiperidinyl)imino]-bis-[ethanol]; poly((6-morpholine-S-triazine-2,4-diyl)(2,2,6,6-tetramethyl-4-piperidinyl)-iminohexamethylene-(2,2,6,6-tetramethyl-4-piperidinyl)-imino); 5-(2,2,6,6-tetramethyl-4-piperidinyl)-2-cycloundecyloxazole); 8-acetyl-3-dodecyl-7,7,9, 9-tetramethyl-1,3,8-triazaspiro(4,5)decane-2,4-dione; polymethylpropyl-3-oxy[4(2,2,6,6-tetramethyl)piperidinyl) siloxane; copolymer of α-methylstyrene-N-(2,2,6,6-tetramethyl-4-piperidinyl)maleimide and N-stearylmaleimide; 1,2, 3,4-butanetetracarboxylic acid, polymer with beta,beta,beta', beta'-tetramethyl-2,4,8,10-tetraoxaspiro[5.5]undecane-3,9-diethanol, 1,2,2,6,6-pentamethyl-4-piperidinyl ester; 2,4,8, 10-tetraoxaspiro[5.5]undecane-3,9-diethanol,beta,beta, beta',beta'-tetramethyl-, polymer with 1,2,3,4-butanetetracarboxylic acid, 2,2,6,6-tetramethyl-4-piperidinyl ester; D-glucitol, 1,3:2,4-bis-O-(2,2,6,6-tetramethyl-4-piperidinylidene)-; oligomer of 7-oxa-3,20-diazadispiro[5.1.11.2]heneicosan-21-one,2,2,4,4-tetramethyl-20-(oxiranylmethyl); propanedioic acid, [(4-methoxyphenyl)methylene]-,bis(1,2,2,6,6-pentamethyl-4-piperidinyl) ester; formamide, N,N'-1,6-hexanediylbis[N-(2, 2,6,6-tetramethyl-4-piperidinyl; 1,3,5-triazine-2,4,6-triamine, N,N'''-[1,2-ethanediylbis ff[4,6-bis[butyl(1,2,2,6,6-pentamethyl-4-iperidinyl)amino]-1,3,5-triazine-2-yl] imino]-3,1-propanediyl]]bis[N',N''-dibutyl-N',N''-bis(1,2,2, 6,6-pentamethyl-4-piperidinyl); 1,5-dioxaspiro (5,5) undecane 3,3-dicarboxylic acid, bis (2,2,6,6-tetramethyl-4-piperidinyl) ester; 1,5-dioxaspiro (5,5) undecane 3,3-dicarboxylic acid, bis (1,2,2,6,6-pentamethyl-4-peridinyl) ester; N-2,2,6,6-tetramethyl-4-piperidinyl-N-amino-oxamide; 4-acryloyloxy-1,2,2,6,6-pentamethyl-4-piperidine; 1,3-benzenedicarboxamide,N,N'-bis(2,2,6,6-tetramethyl-4-piperidinyl); 3-dodecyl-1-(2,2,6,6-tetramethyl-4-piperidyl)-pyrrolidin-2,5-dione; 1,3-Propanediamine, N,N-1,2-ethanediylbis-, polymer with 2,4,6-trichloro-1,3,5-triazine, reaction products with N-butyl-2,2,6,6-tetramethyl-4-piperidinamine; 1,1'-(1,2-ethane-di-yl)-bis-(3,3',5,5'-tetra-methyl-piperazinone); 1,1',1'''-(1,3,5-triazine-2,4,6-triyltris ((cyclohexylimino)-2,1-ethanediyl)tris(3,3,5,5-tetramethylpiperazinone); 1,1',1'''-(1,3,5-triazine-2,4,6-triyltris((cyclohexylimino)-2,1-ethanediyl)tris(3,3,4,5,5-tetramethylpiperazinone); 1,2,3,4-Butanetetracarboxylic acid, tetrakis(2,2,6,6-tetramethyl-4-piperidinyl) ester; 1,2,3, 4-Butane-tetra-carboxylic acid, 1,2,3-tris-(1,2,2,6,6-pentamethyl-4-piperidyl)-4-tridecylester; mixture of esters of 2,2, 6,6-tetra-methyl-4-pipiridinol and several fatty acids; Propanedioic acid, [(4-methoxyphenyl)methylene]-,bis(2,2, 6,6-tetramethyl-4-piperidinyl) ester; 3-Dodecyl-1-(2,2,6,6-tetramethyl-4-piperidyl)-pyrrolidin-2,5-dione; 3-Dodecyl-1-(1,2,2,6,6-pentamethyl-4-piperidyl)-pyrrolidin-2,5-dione; 1,2,3,4-Butanetetracarboxylic acid, tetrakis(1,2,2,6,6-pentamethyl-4-piperidinyl)ester; 1,2,3,4-Butane-tetra-carboxylic acid, 1,2,3-tris-(2,2,6,6-tetra-methyl-4-piperidyl)-4-tridecylester; mixture of: 2,2,4,4 tetramethyl-21-oxo-7-oxa-3.20-diazadispiro[5.1.11.2]-heneicosane-20-propionic acid dodecylester and 2,2,4,4 tetramethyl-21-oxo-7-oxa-3.20-diazadispiro[5.1.11.2]-heneicosane-20-propionicacid tetradecylester; Poly[[6-[(1,1,3,3-tetramethylbutyl)amino]-s-triazine-2,4-diyl][2,2,6,6-tetramethyl-4-piperidinyl)-imino] hexamethylene[(2,2,6,6-tetramethyl-4-piperidinyl)imino]]}; 1,3,5-Triazine-2,4,6-triamine, N,N'''-[1,2-ethanediylbis[[[4, 6-bis[butyl(1,2,2,6,6-pentamethyl-4-piperidinyl)amino]-1, 3,5-triazine-2-yl]imino]-3,1-propanediyl]]-bis[N',N''-dibutyl-N',N''-bis(1,2,2,6,6-pentamethyl-4-piperidinyl); Poly[(6-morpholino-s-triazine-2,4-diyl)[1,2,2,6,6-penta-methyl-4-piperidyl)imino]-hexamethylene[(1,2,2,6,6 penta-methyl-4-piperidyl)iminol]1,6-Hexanediamine, N,N'-bis(1,2,2,6,6-pentamethyl-4-pipiridinyl)-, Polymers with morpholine-2,4, 6-trichloro-1,3,5-triazine; Poly-methoxypopyl-3-oxy[4(1,2, 2,6,6-pentamethyl)-piperidinyl]-siloxane; 1,6-Hexanediamine, N,N'-bis(2,2,6,6-tetramethyl-4piperidinyl)-polymer with 2,4,6-trichloro-1,3,5-triazine, reaction products with N-butyl-1-butanamine and N-butyl-2,2,6,6-tetramethyl-4-piperidinamine; reaction products of N,N'-ethane-1,2-diylbis (1,3-propanediamine), cyclohexane, peroxidized 4-butylamino-2,2,6,6-tetramethylpiperidine and 2,4,6-trichloro-1,3,5- triazine; and 1,6-hexanediamine, N,N'-bis(2,2,6,6-tetramethyl-4-piperidinyl)-, polymer with 2,4,6-trichloro-1,3,5-triazine, reaction products with 3-bromo-1-propene, n-butyl-1- butanamine and N-butyl-2,2,6,6-tetramethyl-4-piperidinamine, oxidized, hydrogenated, wherein Hindered Amine Light Stabilizers are the only stabilizers in the artificial medical implant, wherein the artificial medical implant has a cross-link density of 0.09 mol/dm$^3$ or more.

19. The artificial medical implant according to claim 18, wherein the artificial medical implant has been cross-linked by irradiation with gamma rays at a dose between 30 and 250 kGy.

20. The artificial medical implant according to claim 18, wherein the artificial medical implant has been cross-linked by irradiation with gamma rays at a dose between 40 and 130 kGy.

21. The artificial medical implant according to claim 20, wherein the one or more Hindered Amine Light Stabilizers comprise N,N'''-[1,2-ethanediylbis[[[4,6-bis[butyl(1,2,2,6,6-pentamethyl-4-iperidinyl)amino]-1,3,5-triazine-2-yl]

imino]-3,1-propanediyl]]bis[N',N''-dibutyl-N',N''-bis(1,2,2,6,6-pentamethyl-4-piperidinyl) or poly}[[6-[(1,1,3,3-tetramethylbutyl)amino]-s-triazine-2,4-diyl][(2,2,6,6-tetramethyl-4-piperidinyl)imino]-hexamethylene[(2,2,6,6-tetramethyl-4-piperidinyl)imino]]}.

22. An artificial medical implant having a cross-link density of 0.09 mol/dm$^3$ and consisting of (U)HMWPE and poly{[[6-[(1,1,3,3-tetramethylbutyl)amino]-s-triazine-2,4-diyl][(2,2,6,6-tetramethyl-4-piperidinyl)imino]-hexamethylene[(2,2,6,6-tetramethyl-4-piperidinyl)imino]]}.

23. The artificial medical implant of claim 22, wherein the artificial medical implant has been cross-linked by irradiation with gamma rays at a dose between 40 and 130 kGy.

* * * * *